(12) United States Patent
Qadeer

(10) Patent No.: US 10,779,708 B2
(45) Date of Patent: Sep. 22, 2020

(54) OVERTUBES FOR ENDOSCOPES AND RELATED SYSTEMS AND METHODS

(71) Applicant: Mohammed Qadeer, Northfield, IL (US)

(72) Inventor: Mohammed Qadeer, Northfield, IL (US)

(73) Assignee: APPLIED ENDOSOLUTIONS, LLC, Northfield, IL (US)

( * ) Notice: Subject to any disclaimer, the term of this patent is extended or adjusted under 35 U.S.C. 154(b) by 408 days.

(21) Appl. No.: 15/865,987

(22) Filed: Jan. 9, 2018

(65) Prior Publication Data

US 2019/0046015 A1 Feb. 14, 2019

Related U.S. Application Data

(60) Provisional application No. 62/542,542, filed on Aug. 8, 2017.

(51) Int. Cl.
```
A61B 1/00       (2006.01)
A61B 1/018      (2006.01)
A61B 17/00      (2006.01)
```
(52) U.S. Cl.
CPC ...... *A61B 1/00135* (2013.01); *A61B 1/00087* (2013.01); *A61B 1/00098* (2013.01); *A61B 1/018* (2013.01); *A61B 2017/00269* (2013.01); *A61B 2017/00349* (2013.01)

(58) Field of Classification Search
None
See application file for complete search history.

(56) References Cited

U.S. PATENT DOCUMENTS

| | | | |
|---|---|---|---|
| 3,915,157 A | 10/1975 | Mitsui | |
| 4,636,346 A * | 1/1987 | Gold | A61M 25/001 138/109 |
| 6,352,503 B1 | 3/2002 | Matsui et al. | |
| 6,527,753 B2 | 3/2003 | Sekine et al. | |
| 7,169,115 B2 | 1/2007 | Nobis et al. | |
| 8,187,170 B2 | 5/2012 | Naito | |
| 9,565,998 B2 | 2/2017 | Piskun et al. | |

(Continued)

OTHER PUBLICATIONS

"A Novel Flexible Over-tube for Advanced Endoscopic Intervention Under Stabilized Visualization With Adjustable Tissue Traction", https://www.sages.org/meetings/annual-meeting/abstracts-archive/a-novel-flexible-over-tube-for-advanced-endoscopic-intervention-under-stabilized-visualization-with-adjustable-tissue-traction/, 2012, 2 pages.

*Primary Examiner* — Timothy J Neal
(74) *Attorney, Agent, or Firm* — Myers Bigel, P.A.

(57) ABSTRACT

An overtube for use with an endoscope includes a tube body defining a longitudinal axis, a central channel defined in the tube body and extending along or parallel to the longitudinal axis between proximal and distal end portions of the tube body, and first and second side channels defined in the tube body and extending along or parallel to the longitudinal axis between the proximal and the distal end portions of the tube body. The central channel is sized and configured to receive an endoscope. The first and second side channels are circumferentially spaced part from each other and disposed between the central channel and an outer surface of the tube body. Each of the first and second side channels is sized and configured to receive a retraction device, and each has an elongated arcuate cross section or perimeter at the distal end portion of the tube body.

15 Claims, 10 Drawing Sheets

(56) References Cited

U.S. PATENT DOCUMENTS

| | | | |
|---|---|---|---|
| 2007/0173687 A1 | 7/2007 | Shima et al. | |
| 2007/0270643 A1 | 11/2007 | Lu et al. | |
| 2008/0262301 A1* | 10/2008 | Gibbons | A61B 1/01 600/114 |
| 2009/0048486 A1* | 2/2009 | Surti | A61B 1/2736 600/127 |
| 2009/0227843 A1 | 9/2009 | Smith et al. | |
| 2010/0113878 A1* | 5/2010 | Kawano | A61B 1/018 600/123 |
| 2011/0092766 A1* | 4/2011 | Monassevitch | A61B 1/00094 600/104 |
| 2012/0095291 A1 | 4/2012 | Nakajima | |
| 2016/0120395 A1* | 5/2016 | Qi | A61B 1/00135 600/123 |
| 2016/0166343 A1 | 6/2016 | Poon et al. | |
| 2016/0338681 A1 | 11/2016 | Smith et al. | |
| 2017/0105797 A1 | 4/2017 | Mikkaichi | |
| 2017/0360281 A1* | 12/2017 | Ponsky | A61B 1/018 |

* cited by examiner

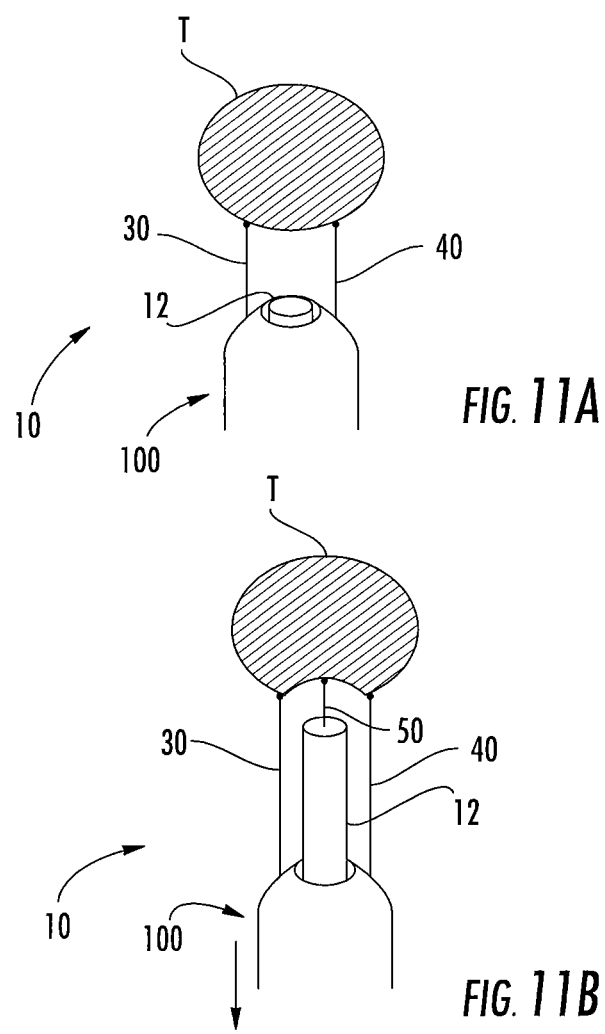

OVERTUBES FOR ENDOSCOPES AND RELATED SYSTEMS AND METHODS

RELATED APPLICATIONS

This application claims priority from U.S. Provisional Application No. 62/542,542, filed Aug. 8, 2017, the disclosure of which is incorporated by reference in its entirety.

BACKGROUND

Endoscopic submucosal dissection (ESD) is an evolving technique in the field of advanced endoscopy. ESD removes large lesions and early cancers of the GI tract, which were previously treated by surgery. Therefore, this is a minimally invasive procedure with significant advantages to patients and payers as extensive, expensive surgeries with well-defined morbidity and mortality are avoided. ESD differs from other tissue resection techniques like endoscopic mucosal resection (EMR) as it removes the tissue en-bloc, and therefore, the specimen appears to be more like a surgically removed specimen rather than the piecemeal tissue resection of EMR. Therefore, the long term outcomes are believed to be better with ESD compared with other endoscopic tissue resection techniques.

Despite its significant advantages, ESD has been slow to be adopted by the gastroenterology community, as it is a technically challenging procedure.

Gastroenterologists are used to working on a two-dimensional platform. Many of their techniques require them to work in a unidirectional manner without triangulation. However, triangulation offers significant advantages for ESD as the tissue can be retracted and dissected which has been shown in multiple studies to reduce the time of procedure and increase the safety of dissection.

SUMMARY

Some embodiments of the present invention are directed to an overtube for use with an endoscope. The overtube includes a tube body defining a longitudinal axis and having opposite proximal and distal end portions, a central channel defined in the tube body and extending along or parallel to the longitudinal axis between the proximal and the distal end portions of the tube body, and first and second side channels defined in the tube body and extending along or parallel to the longitudinal axis between the proximal and the distal end portions of the tube body. The central channel is sized and configured to receive an endoscope. The first and second side channels are circumferentially spaced part from each other and disposed between the central channel and an outer surface of the tube body. Each of the first and second side channels is sized and configured to receive a retraction device, and each of the first and second side channels has an elongated arcuate cross section or perimeter at the distal end portion of the tube body.

Some other embodiments of the present invention are directed to an endoscope system. The system includes an overtube, an endoscope, a first retraction device, and optionally a second retraction device. The overtube includes a tube body defining a longitudinal axis and having opposite proximal and distal end portions, a central channel defined in the tube body and extending along or parallel to the longitudinal axis between the proximal and the distal end portions of the tube body, and first and second side channels defined in the tube body and extending along or parallel to the longitudinal axis between the proximal and the distal end portions of the tube body. The first and second side channels are circumferentially spaced part from each other and disposed between the central channel and an outer surface of the tube body, and each of the first and second side channels has an elongated arcuate cross section or perimeter at the distal end portion of the tube body. The endoscope is received in the central channel. The first retraction device is received in the first side channel. Where used, the second retraction device is received in the second side channel. The overtube is slidable relative to and independent of the endoscope, the first retraction device, and the second retraction device.

Some other embodiments of the present invention other embodiments of the present invention are directed to a method for performing endoscopic submucosal dissection in a GI tract of a patient. The method includes providing an endoscope system. The endoscope system includes a tube body defining a longitudinal axis and having opposite proximal and distal end portions, a central channel defined in the tube body and extending along or parallel to the longitudinal axis between the proximal and the distal end portions of the tube body, first and second side channels defined in the tube body and extending along or parallel to the longitudinal axis between the proximal and the distal end portions of the tube body, an endoscope received in the central channel of the tube body, a first retraction device received in the first side channel of the tube body, a second retraction device received in the second side channel of the tube body, and a dissection device received in a lengthwise instrument channel defined in the endoscope. The first and second side channels are circumferentially spaced part from each other and disposed between the central channel and an outer surface of the tube body, and each of the first and second side channels has an elongated arcuate section at the distal end portion of the tube body. The method includes: receiving the endoscope system in a lumen of the GI tract of a patient; advancing the first retraction device in the first side channel of the tube body and second retraction device in the second side channel of the tube body such that a distal end portion of the first retraction device extends from the distal end portion of the tube body and a distal end portion of the second retraction device extends from the distal end portion of the tube body; sliding the distal end portion of the first retraction device in the elongated arcuate section of the first side channel and/or sliding the distal end portion of the second retraction device in the elongated arcuate section of the second side channel; grasping and retracting a lesion in the lumen using the first and second retraction devices; dissecting the grasped lesion using the dissection device; and sliding the tube body away from the tissue before, during, and/or after dissecting the grasped lesion.

Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIGS. 11A and 12A schematically illustrate retraction devices of the endoscope system of FIG. 1 engaging and retracting a target lesion or tissue.

FIGS. 11B and 12B schematically illustrate a dissection device of the endoscope system of FIG. 1 dissecting a tissue and an overtube of the endoscope system of FIG. 1 being pulled back or withdrawn to provide triangulation according to embodiments of the present invention.

DETAILED DESCRIPTION

Figure 1:
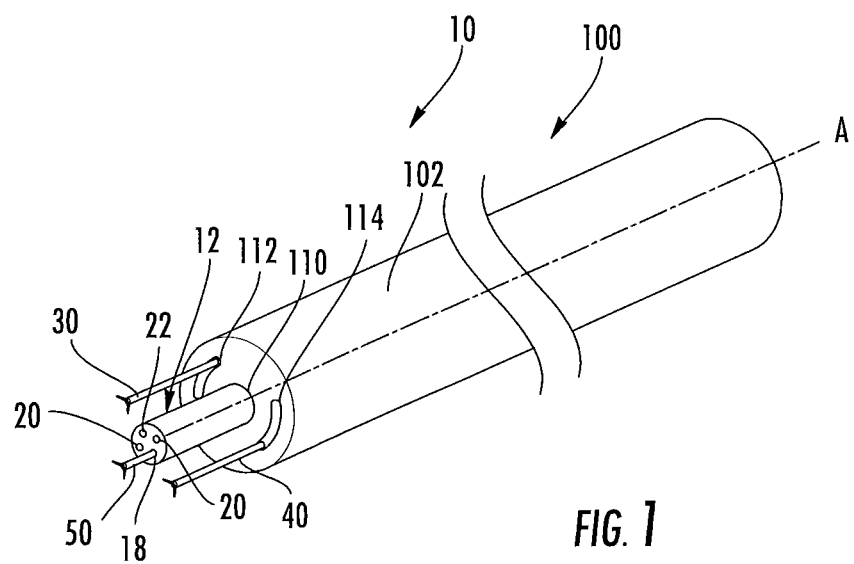
FIG. 1 is a perspective view of an endoscope system according to some embodiments of the present invention.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Figure 2:
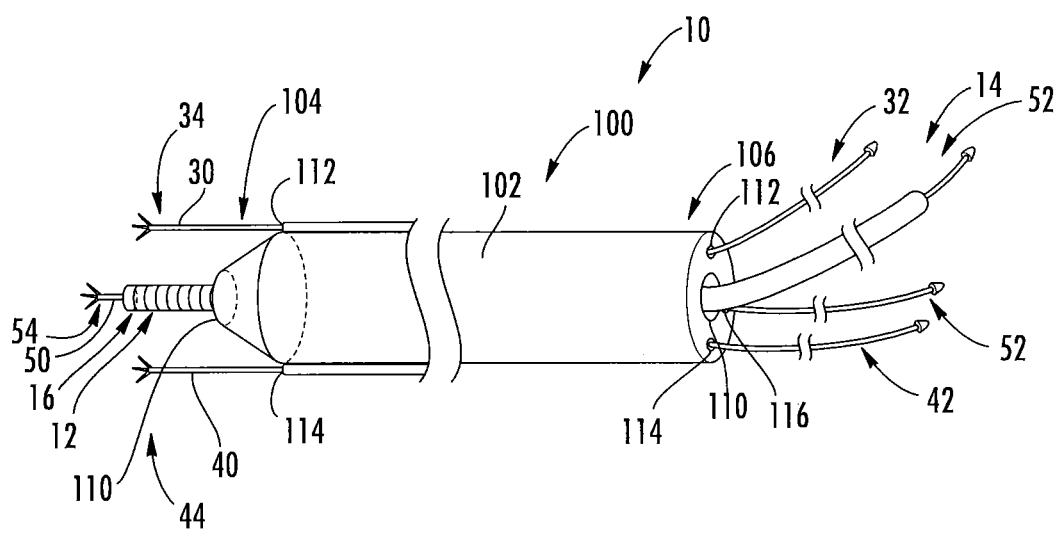
FIG. 2 is a schematic perspective view of the endoscope system of FIG. 1.

An endoscope system 10 according to some embodiments is illustrated in FIGS. 1 and 2. The system 10 includes a guide tube or overtube 100 (which may also be referred to herein as an "ESD platform"). The overtube 100 has a body 102. The overtube body (or tube body) 102 defines a longitudinal axis A and includes opposite proximal and distal end portions 104, 106.

A central channel or passageway 110 is defined in the overtube body 102. First and second side or peripheral channels or passageways 112, 114 are also defined in the overtube body 102.

An endoscope 12 may be received in the central channel 110 of the overtube 100. The endoscope 12 includes opposite proximal and distal end portions 14, 16. An instrument channel 18 (e.g., working channel) extends lengthwise through the endoscope 12 between the proximal and distal end portions 14, 16. The endoscope 12 may include one or more illumination windows 20 and an observation window 22 at the distal end portion 16 thereof.

A first retraction device 30 may be received in the first side channel 112 of the overtube 100. The first retraction device 30 includes opposite proximal and distal end portions 32, 34. An operator may control or manipulate the first retraction device 30 at the proximal end portion 32 as understood by those skilled in the art.

A second retraction device 40 may be received in the second side channel 114 of the overtube 100. The second retraction device 40 includes opposite proximal and distal end portions 42, 44. An operator may control or manipulate the second retraction device 40 at the proximal end portion 42 as understood by those skilled in the art.

A dissection device 50 may be received in the instrument channel 18 of the endoscope 12. The dissection device 50 includes opposite proximal and distal end portions 52, 54. An operator may control or manipulate the dissection device 50 at the proximal end portion 52 as understood by those skilled in the art.

The overtube 100 may be moveable or slidable relative to the endoscope 12, the first retraction device 30, and/or the second retraction device 40 as described in more detail below.

The overtube 100 according to embodiments of the invention will now be described in greater detail with reference to FIGS. 3-6. The overtube body 102 may be formed of a flexible material such as a polymeric, plastic, and/or silastic material. The overtube body 102 may be transparent or translucent. The overtube body 102 has a diameter D1 (FIG. 3) and a length L (FIG. 4). According to some embodiments, the length L is between 25 and 150 cm. According to some embodiments, the diameter D1 is between 15 and 25 mm.

Referring to FIGS. 3-6, the central channel 110 extends along the longitudinal axis A between the proximal and distal end portions 104, 106 of the overtube body 102. Specifically, the central channel 110 has a proximal end 110A at a proximal end 120 of the overtube body 102 and a distal end 110B at a distal end 122 of the overtube body. According to some embodiments, the central channel 110 has a diameter D2 of between 10 and 15 mm.

The first side channel 112 extends along or parallel to the longitudinal axis A between the proximal and distal end portions 104, 106 of the overtube body 102. Specifically, the first side channel 112 has a proximal end 112A at the proximal end 120 of the overtube body 102 and a distal end 112B at the distal end 122 of the overtube body.

The second side channel 114 extends along or parallel to the longitudinal axis A between the proximal and distal end portions 104, 106 of the overtube body 102. Specifically, the second side channel 114 has a proximal end 114A at the proximal end 120 of the overtube body 102 and a distal end 114B at the distal end 122 of the overtube body.

Figure 3:
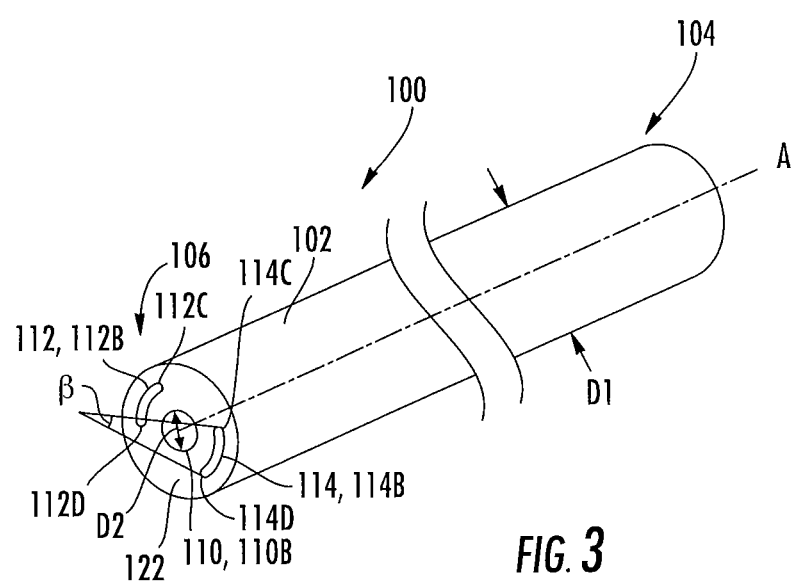
FIG. 3 is a perspective view of an overtube used with the endoscope system of FIG. 1 according to some embodiments.
Figure 4:
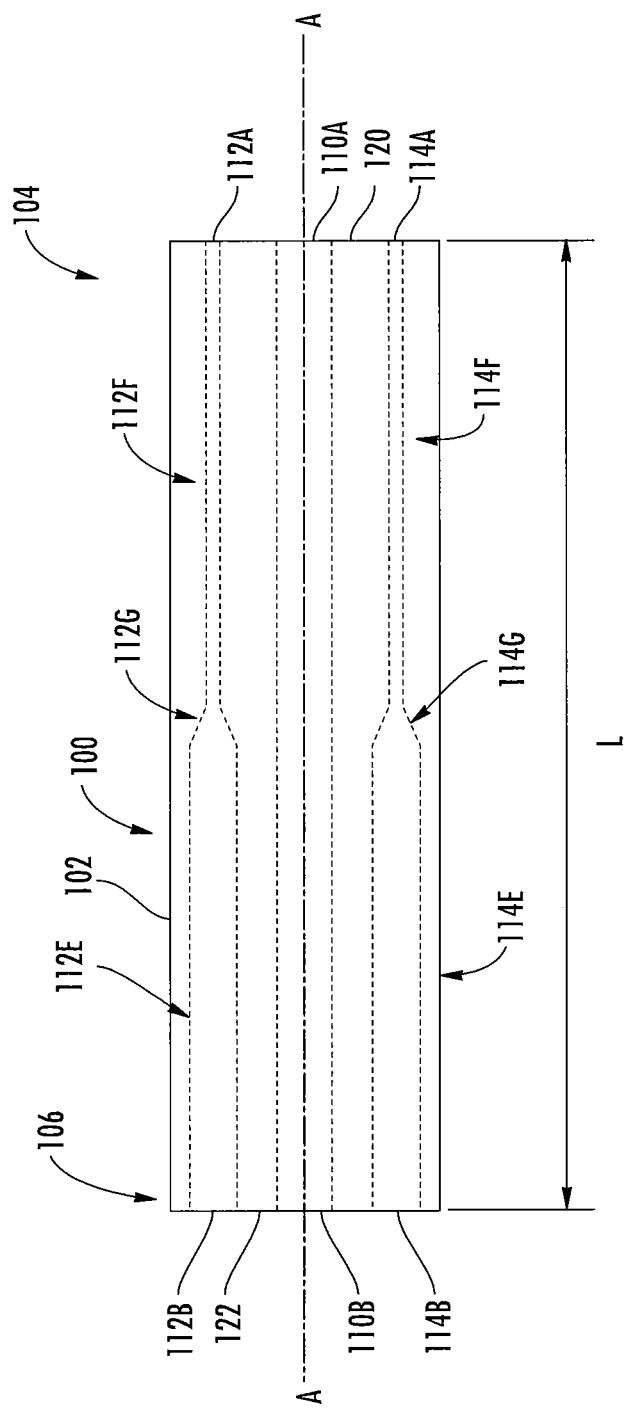
FIG. 4 is a schematic side view of the overtube of FIG. 3.
Figure 6:
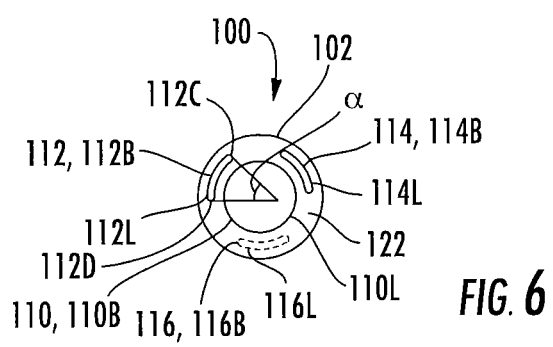
FIG. 6 is a distal end view of the overtube of FIG. 3.

Referring to FIG. 3, each of the first and second side channels 112, 114 has an arcuate cross section or perimeter at the distal end portion 106 of the overtube body 102 (e.g., in a plane perpendicular to the longitudinal axis A). The first side channel 112 is elongated and includes opposite first and second end surfaces 112C, 112D. Referring to FIG. 6, an angle α may be defined between the first and second end surfaces 112C, 112D. The angle α may be at the center of curvature of the side channel 112 and may be between 50 degrees and 70 degrees and, in some embodiments, is about 60 degrees.

Similarly, the second side channel 114 is elongated and includes opposite first and second end surfaces 114C, 114D. Referring to FIG. 3, an angle β may be defined between the first and second end surfaces 114C, 114D. The angle α may be at the center of curvature of the side channel 114 and may be between 50 degrees and 70 degrees and, in some embodiments, is about 60 degrees. As described in more detail below, the configuration with the elongated arcuate side channels allows the retraction device received in the side channel to translate along the elongated arcuate profile of the side channel between the first and second end surfaces thereof.

Referring to FIG. 6, the first side channel 112 may extend from the 9 o'clock position to the 11 o'clock position at the overtube body distal end 122. The second side channel 114 may extend from the 1 o'clock position to the 3 o'clock position at the overtube body distal end 122. This provides about 60 degrees of freedom of movement for a retraction device extending from the distal ends 112B, 114B of the first and second side channels 112, 114.

Figure 5:
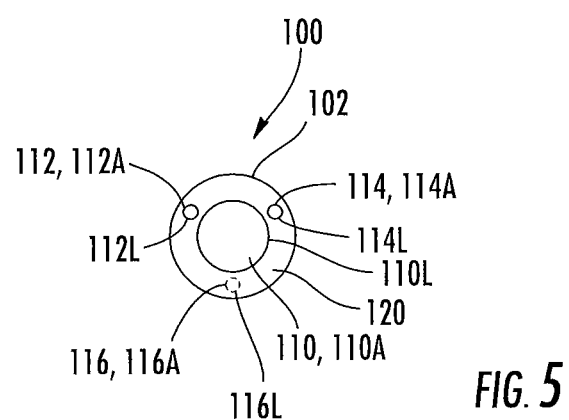
FIG. 5 is a proximal end view of the overtube of FIG. 3.

Referring to FIGS. 4-6, the first side channel 112 may transition from having an arcuate cross section at the distal end portion 106 of the body 102 to a smaller round or circular cross section at the proximal end portion 104 of the body 102. The first side channel 112 may include an arcuate section 112E and a round section 112F. The first side channel 112 may transition from the arcuate section 112E to the round section 112F at a transition point or region 112G (FIG. 4). According to some embodiments, the transition point 112G is between 1 and 2 cm from the proximal end 120 of the body 102. According to some other embodiments, the transition point 112G is between 1 and 2 cm from the distal end 122 of the body 102.

Similarly, the second side channel 114 may transition from having an arcuate cross section at the distal end portion 106 of the body 102 to a round or circular cross section at the proximal end portion 104 of the body 102. The second side channel 114 may include an arcuate section 114E and a round section 114F. The second side channel 114 may transition from the arcuate section 114E to the round section 114F at a transition point or region 114G (FIG. 4). According to some embodiments, the transition point 114G is between 1 and 2 cm from the proximal end 120 of the body 102. According to some other embodiments, the transition point 114G is between 1 and 2 cm from the distal end 122 of the body 102.

The round sections of the side channels may provide stability for the retraction devices received therein. For example, the round section of the side channel may have a diameter that is about the same or slightly greater than a diameter of a shaft of the retraction device.

The diameter of the proximal ends 112A, 114A and/or the round sections 112F, 114F of the first and second side channels 112, 114 may be between 7 and 10 French (2.3 mm and 3.3 mm).

Referring to FIGS. 5 and 6, the central channel 110 may be defined by a central channel layer 110L. The first and second side channel 112, 114 may be defined by first and second channel layers 112L, 114L, respectively. The channel layers 110L, 112L, and/or 114L may be formed of a polymeric, plastic, and/or silastic material. The channel layers 110L, 112L, and/or 114L may each be surrounded by the overtube body 102. For example, the overtube body may be molded over the channel layers 110L, 112L, and/or 114L. The channel layers 110L, 112L, and/or 114L may have increased rigidity relative to the overtube body 102. In this regard, the channels 110, 112, and/or 114 may facilitate easier insertion and manipulation of endoscopes and/or retraction devices received therein. According to some embodiments, an inner surface of the channels 110, 112, and/or 114 is coated with a hydrophilic material to further facilitate sliding of the instruments in the channels.

Figure 7:
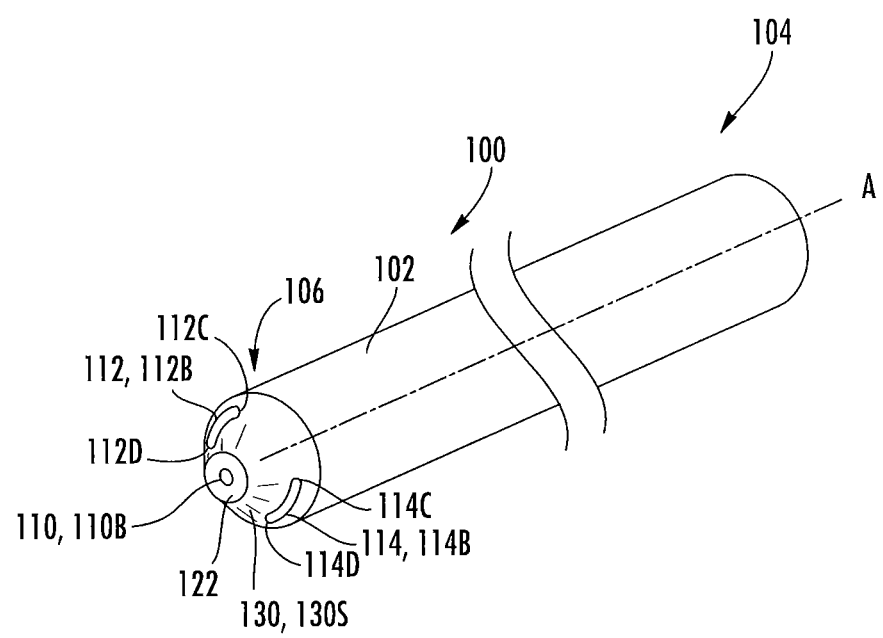
FIG. 7 is a perspective view of an overtube used with the endoscope system of FIG. 1 according to some other embodiments of the present invention.
Figure 8:
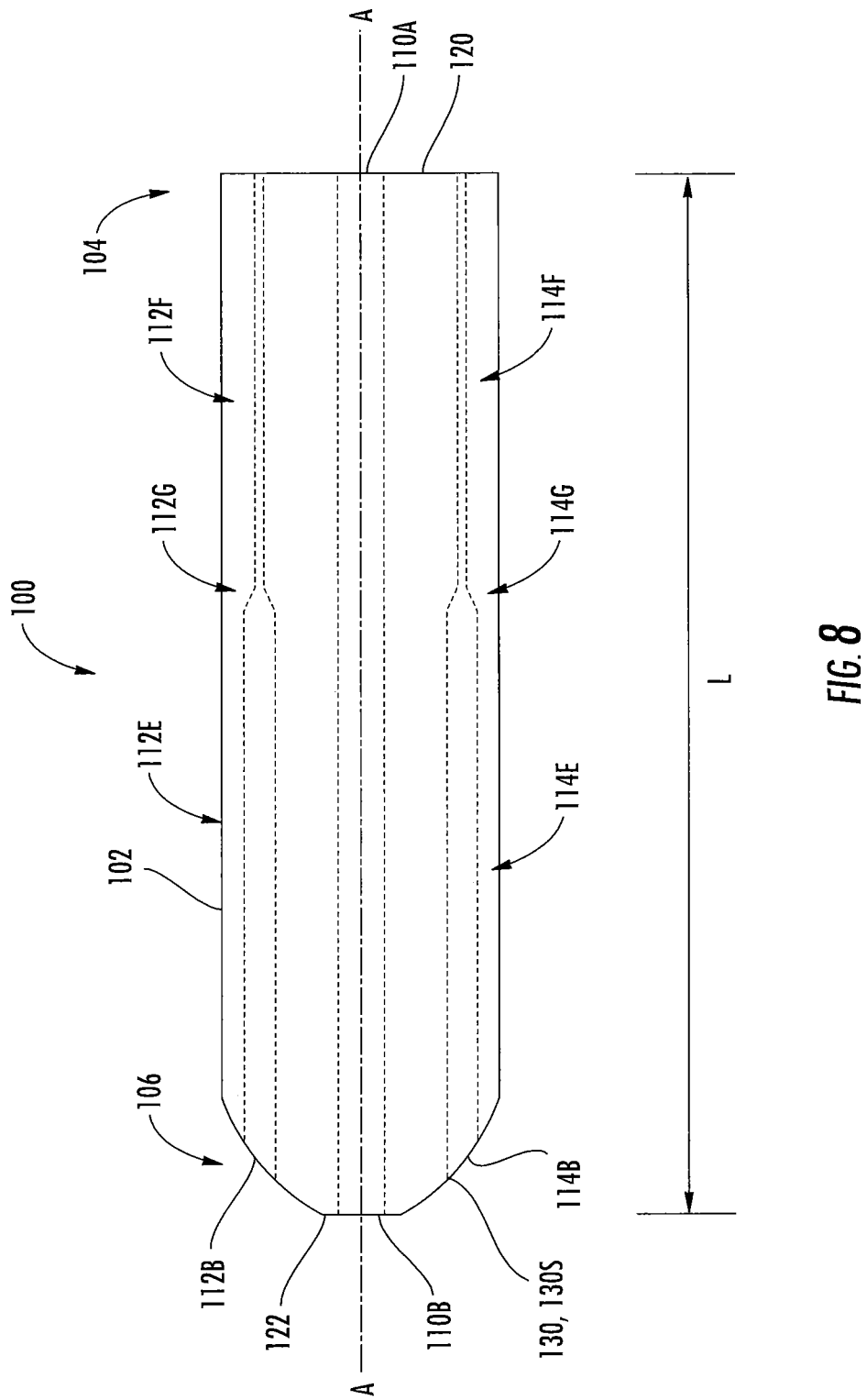
FIG. 8 is a schematic side view of the overtube of FIG. 7.
Figure 9:
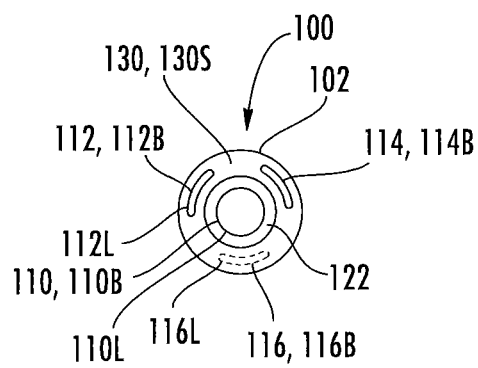
FIG. 9 is a distal end view of the overtube of FIG. 7.

FIGS. 7-9 illustrate the overtube 100 according to some other embodiments, with the primary difference being at the distal end portion 106 of the overtube body 102. Specifically, referring to FIG. 7, the distal end portion 106 of the overtube body 102 may include a smooth tapered portion 130. The tapered portion 130 may include a tapered outer surface 130S.

FIG. 8 is a schematic side view of the overtube 100 and illustrates that the first and second side channels 112, 114 may extend from the tapered surface 130S to the proximal end 120 of the overtube body 102.

FIG. 9 is a distal end view of the overtube 100 of FIG. 7. It is noted that the proximal end view of the overtube of FIG. 7 is the same or similar to as shown in FIG. 5.

It is contemplated that more than two arcuate side channels may be defined in the overtube 100. For example, a third side channel 116 is shown in dashed lines in FIGS. 5, 6 and 9. The third side channel 116 may extend from the 5 o'clock position to the 7 o'clock position at the overtube body distal end 122. The third side channel 116 may include an arcuate section and a round or circular section with a transition point or section therebetween as described above in reference to the side channels 112, 114. The third side channel 116 may be defined by a third channel layer 116L which may have increased rigidity relative to the overtube body 102. An inner surface of the third side channel 116 may be coated with a hydrophilic material.

Figure 10:
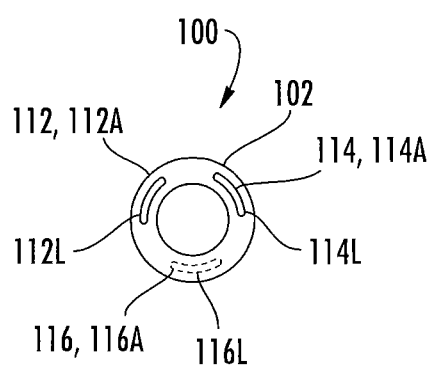
FIG. 10 is a proximal end view of the overtube of FIG. 3 or FIG. 7 according to some other embodiments.

Referring to FIG. 10, in some embodiments, the side channels 112, 114, and/or 116 may have an arcuate cross section along the entire length of the overtube body 102. In other words, the side channels 112, 114, and/or 116 may not have a transition point in the manner described above.

Referring to FIG. 1, in use, the endoscope 12 is passed through the central channel 100 of the overtube 100, the first retraction device 30 is passed through the first side channel 112 of the overtube 100, and/or the second retraction device is passed through the second side channel 114 of the overtube 100. The endoscope 12, the first and second retraction devices 30, 40, and the overtube 100 can all move independently of one another. The retraction devices 30, 40 can each have 60 degrees of freedom of movement at the distal end due to the elongated arcuate side channels 112, 114.

Figure 12A:
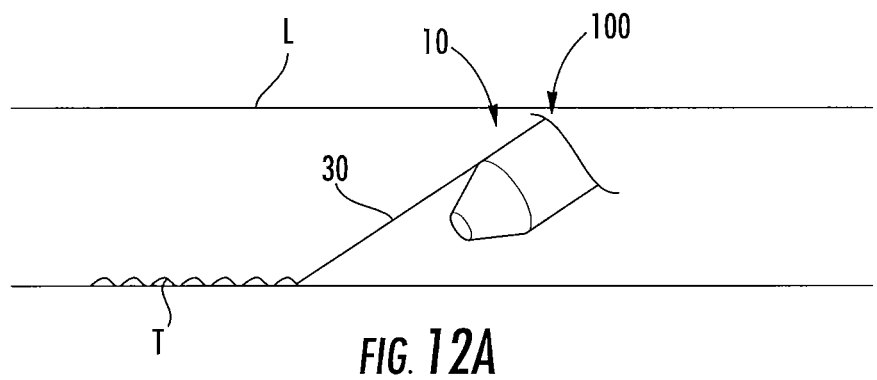
Figure 12B:
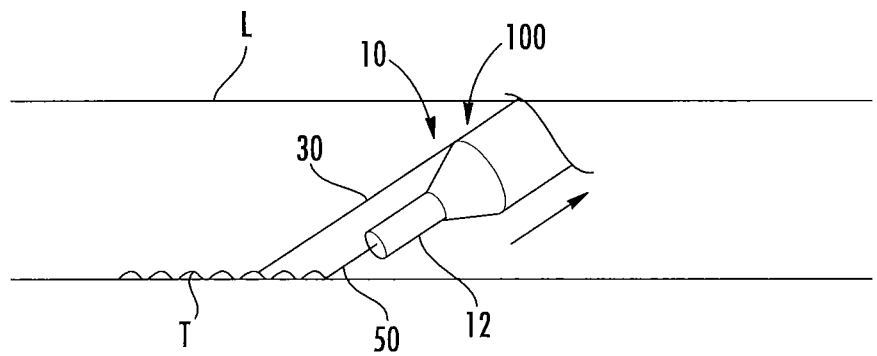

Referring to FIGS. 11A and 12A, the endoscope system 10 is received in a lumen L of the GI tract of a patient. The retraction devices 30, 40 hold a lesion or tissue T to be dissected and retract it from the base. Referring to FIGS. 1, 11B, and 12B, the dissection device 50 is passed through the instrument channel 18 of the endoscope 12 and is advanced for dissection. Referring to FIGS. 11B and 12B, the overtube 100 is withdrawn or slid back away from the tissue T. The length of withdrawal determines the degree of triangulation. The variable and adjustable triangulation aids in dissection.

Embodiments of the present invention provide elongated arcuate side channels that allow, for example, 60 degrees of freedom of movement for the retraction devices. The overtube can have free movement over the endoscope to provide adjustable triangulation by varying the amount or length of overtube withdrawal. The triangulation is obtained by sliding the overtube in relation to the other devices. This form of triangulation may result in faster and safer dissection. Stated somewhat differently, embodiments of the present invention allow for adjusting the tube body distance from the tissue by independent sliding of the tube body relative to other devices, and therefore, generating a triangulation that aids in faster dissection of the grasped lesion. The easy and independent slidability of the different devices results in maintaining a constant traction of the tissue and varying triangulation of the devices that aids in faster dissection.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

What is claimed is:

1. An overtube for use with an endoscope, the overtube comprising:
   a tube body defining a longitudinal axis and having opposite proximal and distal end portions;
   a central channel defined in the tube body and extending along or parallel to the longitudinal axis between the proximal and the distal end portions of the tube body, the central channel sized and configured to receive an endoscope;
   first and second side channels defined in the tube body and extending along or parallel to the longitudinal axis between the proximal and the distal end portions of the tube body, the first and second side channels being circumferentially spaced part from each other and disposed between the central channel and an outer surface of the tube body, each of the first and second side channels sized and configured to receive a retraction device, wherein each of the first and second side channels has an elongated arcuate cross section or perimeter at the distal end portion of the tube body,
   wherein each of the first and second side channels has a round cross section or perimeter at the proximal end portion of the tube body.

2. The overtube of claim 1 wherein the tube body surrounds each of the central channel, the first side channel, and the second side channel.

3. The overtube of claim 2 wherein each of the central channel, the first side channel, and the second side channel are formed of material that has increased rigidity relative to the tube body.

4. The overtube of claim 1 wherein each of the first and second side channels comprises an arcuate section having an arcuate cross section or perimeter and a round section having a round cross section or perimeter, and wherein each of the first and second side channels comprises a transition point between the arcuate section and the round section.

5. The overtube of claim 1 wherein:
   the distal end portion of the tube body comprises a tapered portion including a tapered outer surface;
   the central channel terminates at the distal end of the tube body; and
   the first and second side channels each terminate at the tapered outer surface of the tube body.

6. The overtube of claim 1 wherein each of the first and second side channels surrounds about 60 degrees of the central channel at the distal end portion of the tube body.

7. An endoscope system comprising:
   an overtube comprising:
      a tube body defining a longitudinal axis and having opposite proximal and distal end portions;
      a central channel defined in the tube body and extending along or parallel to the longitudinal axis between the proximal and the distal end portions of the tube body; and
      first and second side channels defined in the tube body and extending along or parallel to the longitudinal axis between the proximal and the distal end portions of the tube body, the first and second side channels being circumferentially spaced part from each other and disposed between the central channel and an outer surface of the tube body, wherein each of the first and second side channels has an elongated arcuate cross section or perimeter at the distal end portion of the tube body, and wherein each of the first and second side channels has a round cross section or perimeter at the proximal end portion of the tube body;
   an endoscope received in the central channel;
   a first retraction device received in the first side channel; and
   optionally a second retraction device received in the second side channel;

wherein the overtube is slidable relative to and independent of the endoscope, the first retraction device, and the second retraction device.

8. The system of claim 7, wherein the endoscope has a lengthwise instrument channel defined therein, the system further comprising a dissection device received in the instrument channel.

9. The system of claim 7 wherein the tube body surrounds each of the central channel, the first side channel, and the second side channel.

10. The system of claim 7 wherein each of the central channel, the first side channel, and the second side channel are formed of material that has increased rigidity relative to the tube body.

11. The system of claim 7 wherein each of the first and second side channels comprises an arcuate section having an arcuate cross section or perimeter and a round section having a round cross section or perimeter, and wherein each of the first and second side channels comprises a transition point between the arcuate section and the round section.

12. The system of claim 7 wherein:
the distal end portion of the tube body comprises a tapered portion including a tapered outer surface;
the central channel terminates at the distal end of the tube body; and
the first and second side channels each terminate at the tapered outer surface of the tube body.

13. The system of claim 7 wherein each of the first and second side channels surrounds about 60 degrees of the central channel at the distal end portion of the tube body.

14. The system of claim 7 comprising the second retraction device received in the second side channel.

15. A method for performing endoscopic submucosal dissection in a GI tract of a patient, the method comprising:
providing an endoscope system comprising:
a tube body defining a longitudinal axis and having opposite proximal and distal end portions;
a central channel defined in the tube body and extending along or parallel to the longitudinal axis between the proximal and the distal end portions of the tube body;
first and second side channels defined in the tube body and extending along or parallel to the longitudinal axis between the proximal and the distal end portions of the tube body, the first and second side channels being circumferentially spaced part from each other and disposed between the central channel and an outer surface of the tube body, wherein each of the first and second side channels has an elongated arcuate section at the distal end portion of the tube body, and wherein each of the first and second side channels has a round cross section or perimeter at the proximal end portion of the tube body;
an endoscope received in the central channel of the tube body;
a first retraction device received in the first side channel of the tube body;
a second retraction device received in the second side channel of the tube body; and
a dissection device received in a lengthwise instrument channel defined in the endoscope;
receiving the endoscope system in a lumen of the GI tract of a patient;
advancing the first retraction device in the first side channel of the tube body and second retraction device in the second side channel of the tube body such that a distal end portion of the first retraction device extends from the distal end portion of the tube body and a distal end portion of the second retraction device extends from the distal end portion of the tube body;
sliding the distal end portion of the first retraction device in the elongated arcuate section of the first side channel and/or sliding the distal end portion of the second retraction device in the elongated arcuate section of the second side channel;
grasping and retracting a lesion in the lumen using the first and second retraction devices;
dissecting the grasped lesion using the dissection device; and
sliding the tube body away from the tissue before, during, and/or after dissecting the grasped lesion.

* * * * *